(12) United States Patent
Horridge et al.

(10) Patent No.: US 11,459,679 B2
(45) Date of Patent: Oct. 4, 2022

(54) NONWOVEN FABRIC

(71) Applicant: ADVANCED MEDICAL SOLUTIONS LIMITED, Winsford (GB)

(72) Inventors: David Horridge, Sandbach (GB); Colin Bradford, Keighley (GB)

(73) Assignee: ADVANCED MEDICAL SOLUTIONS LIMITED, Winsford (GB)

( * ) Notice: Subject to any disclaimer, the term of this patent is extended or adjusted under 35 U.S.C. 154(b) by 79 days.

(21) Appl. No.: 15/720,206

(22) Filed: Sep. 29, 2017

(65) Prior Publication Data
US 2018/0094369 A1    Apr. 5, 2018

(30) Foreign Application Priority Data

Sep. 30, 2016   (GB) ..................... 1616618

(51) Int. Cl.
| | |
|---|---|
| *D04H 1/46* | (2012.01) |
| *A61L 15/22* | (2006.01) |
| *A61L 15/28* | (2006.01) |
| *D01F 9/04* | (2006.01) |
| *D04H 1/485* | (2012.01) |
| *D04H 18/02* | (2012.01) |

(52) U.S. Cl.
CPC .......... *D04H 1/485* (2013.01); *A61L 15/225* (2013.01); *A61L 15/28* (2013.01); *D01F 9/04* (2013.01); *D04H 1/46* (2013.01); *D04H 18/02* (2013.01)

(58) Field of Classification Search
None
See application file for complete search history.

(56) References Cited

U.S. PATENT DOCUMENTS

| | | | | |
|---|---|---|---|---|
| 5,677,028 | A | * | 10/1997 | Ravella .................... B32B 5/24 428/102 |
| 6,080,420 | A | | 6/2000 | Qin et al. |
| 6,231,555 | B1 | | 5/2001 | Lynard et al. |
| 6,403,505 | B1 | | 6/2002 | Groitzsch et al. |
| 6,726,670 | B2 | | 4/2004 | Almberg et al. |
| 7,358,202 | B2 | | 4/2008 | Hartman et al. |
| 7,427,434 | B2 | | 9/2008 | Busam et al. |

(Continued)

FOREIGN PATENT DOCUMENTS

| | | |
|---|---|---|
| DE | 20 2009 000 775 U1 | 4/2009 |
| EP | 1 076 539 B1 | 8/2003 |

(Continued)

OTHER PUBLICATIONS

Espacenet translation of JP-2002020957-A, accessed on Jun. 17, 2020. (Year: 2002).*

(Continued)

*Primary Examiner* — Jeremy R Pierce
*Assistant Examiner* — Christine X Nisula
(74) *Attorney, Agent, or Firm* — Nixon & Vanderhye P.C.

(57) ABSTRACT

The present invention relates to a bonded nonwoven fabric generally including absorbent staple fibres and having bonding stripes of relatively high fibre entanglement density extending along the fabric and into the fabric from at least one face thereof. A method of producing a bonded nonwoven fabric suitable for use as an absorbent layer in a wound dressing is also described.

19 Claims, 3 Drawing Sheets

(56) References Cited

U.S. PATENT DOCUMENTS

| | | | |
|---|---|---|---|
| 7,682,686 B2 | 3/2010 | Curro et al. | |
| 7,763,339 B2 | 7/2010 | Groitzsch et al. | |
| 8,956,477 B2 | 12/2015 | Schoenbeck | |
| 9,771,675 B2 | 9/2017 | Altshuler et al. | |
| 10,076,451 B2 | 9/2018 | Giovanni et al. | |
| 10,307,311 B2 | 6/2019 | Sheldon et al. | |
| 10,492,958 B2 | 12/2019 | Matsui et al. | |
| 10,813,799 B2 | 10/2020 | Ducker | |
| 10,821,037 B2 | 11/2020 | Isele et al. | |
| 10,982,362 B2 | 4/2021 | Ellingson et al. | |
| 2003/0118780 A1 | 6/2003 | Adam et al. | |
| 2004/0219854 A1 | 11/2004 | Groitzsch et al. | |
| 2008/0021424 A1 | 1/2008 | Erdman | |
| 2011/0250413 A1 | 10/2011 | Lu et al. | |
| 2012/0316532 A1 | 12/2012 | McCormick | |
| 2013/0232712 A1 | 9/2013 | Kawai et al. | |
| 2013/0296818 A1* | 11/2013 | Bradford | A61F 13/00029 604/368 |
| 2015/0335492 A1* | 11/2015 | Tao | A61F 13/00008 602/43 |
| 2019/0262195 A1 | 8/2019 | Glaug et al. | |
| 2020/0214911 A1 | 7/2020 | Nakaoka et al. | |

FOREIGN PATENT DOCUMENTS

| | | | | |
|---|---|---|---|---|
| EP | 1 873 292 B1 | | 11/2009 | |
| EP | 2 644 761 A1 | | 10/2013 | |
| EP | 3 119 361 B1 | | 6/2018 | |
| EP | 3 322 391 B1 | | 2/2020 | |
| EP | 3 437 601 B1 | | 10/2020 | |
| EP | 3 437 602 B1 | | 3/2021 | |
| GB | 1 510 580 | | 5/1978 | |
| GB | 1 534 979 A | | 12/1978 | |
| GB | 2 114 054 A | | 8/1983 | |
| GB | 2401879 A | * | 11/2004 | A61F 13/00042 |
| GB | 2489947 A | * | 10/2012 | A61F 13/00029 |
| GB | 2554651B B | | 8/2019 | |
| JP | 2002-020957 | | 1/2002 | |
| JP | 2002-369782 | | 12/2002 | |
| JP | 4543196 B2 | | 7/2010 | |
| JP | 2011-21310 A | | 2/2011 | |
| WO | 2018/123638 A1 | | 7/2018 | |
| WO | 2019/038451 A1 | | 2/2019 | |

OTHER PUBLICATIONS

Aquanoba (RTM) http://www.medtrade.co.uk/woundprod_gelfibre.htm (cited in Jan. 20, 2017 Search and Examination Report issued in GB Application No. 1616618.3, copy retrieved Jan. 16, 2018).

Jan. 20, 2017 Search and Examination Report issued in GB Application No. 1616618.3.

Aug. 3, 2018 Examination Report under Section 18(3) issued in GB Application No. GB1616618.3.

Feb. 15, 2018 Extended European Search Report issued in European Application No. 17194246.9.

* cited by examiner

NONWOVEN FABRIC

This application claims priority to GB Patent Application No. 1616618.3 filed 30 Sep. 2016, the entire contents of which is hereby incorporated herein by reference.

The present invention relates to a bonded, nonwoven fabric comprised of absorbent staple fibres, optionally in conjunction with non-absorbent staple fibres. The fabric of the invention has particular (but not exclusive) use as an absorbent layer in a wound dressing.

BACKGROUND

The production of bonded nonwoven materials from staple fibres is a well-established technology. Briefly, the method involves three main steps, which can be classified as (1) fibre preparation, (2) web formation, and (3) bonding. In step (1), a mass of staple fibres is subjected to an operation (also known as "opening") which involves separating clumps of staple fibres into individual fibres, usually by a course combing action. The staple fibres may have been obtained by cutting continuous filaments into specified lengths or may occur naturally as fibres of specific lengths, as in the case of cotton. In this "preparation" stage, more than one type of fibre can be blended together, if desired.

In step (2), a web is formed from the "opened" fibres resulting from step (1). Step (2) is generally effected by air-laying or by carding. In air laying, the fibres are further opened and then drawn by vacuum onto the surface of a rotating drum to create a sheet of fibres which is then withdrawn from the drum by a conveyor (resulting in a continuous web). Typical web weights obtained by air laying are 100-300 g m$^{-2}$. Carding is a finer combing action to separate fibres and create a coherent, lightweight web. The fibres are largely oriented in the length direction (i.e. machine direction of the produced web). Typical web weights produced by carding are 5-25 g m$^{-2}$. Webs in this weight range typically need to be made heavier to provide good absorbency. The weight can be increased by having multiple cards in line and laying the webs on top of each other. An alternative approach is cross lapping, where overlapping layers of the lightweight, carded web are overlapped to build up the overall weight to the required level. The cross lapping action effectively re-orientates the web through 90° so that the fibres within the web (which previously ran in the machine direction) are now oriented across the width of the web. Irrespective of whether air-laying or carding is employed, the resulting web can be considered to be an unbonded web.

In step (3) there is bonding of the fibres in the web to provide a more coherent structure. Bonding may be by thermal or chemical means or by entanglement. In thermal bonding, some or all of the fibres melt when exposed to heat, e.g. applied by a laminator, hot air oven or calendar. This causes the fibres to stick together creating a bonded web.

In chemical bonding, a (usually aqueous based) solution containing a polymeric binder is applied to the unbonded web. Application of the solution may, for example, be by printing, dipping or as a foamed solution. The solvent is then removed by drying so that the polymeric binder remaining serves to bond the fibres together.

In bonding by entanglement, the fibres in the web are physically entangled together. This may be achieved by the use of high pressure water jets (referred to as hydro-entangling or spun lacing) or by barbed needles, the latter technique being referred to as needling or felt making. In needling, the barbed tips of an array of barbed needles are reciprocated into and out of the web, taking fibres from the surface into the interior of the web, thereby entangling the fibres to create a felt. Generally, the needles only take fibres on their way into the web and do not have any effect on their way out.

Needling can be applied from one or both sides of the web. The controls in needling are the type and gauge of needles used, the quantity of needles, the pattern of the needles, the needling speed, and the penetration depth of the needles (which may be only partway through the web).

As the overall level of needling is increased, the strength of the final nonwoven fabric (felt) increases, but the absorbency is reduced. This reduction in absorbency is due to the bonded nonwoven fabric (felt) being more compressed and having less internal space to absorb fluid. This reduction in absorbency can be compensated by increasing the weight of the felt, but the weight increase may be unacceptable.

BRIEF SUMMARY

It is therefore an object of the invention to obviate or mitigate the abovementioned disadvantages.

According to a first aspect of the present invention there is provided a bonded nonwoven fabric comprised of absorbent staple fibres and having bonding stripes of relatively high fibre entanglement density extending along the fabric and into the fabric from at least one face thereof, said stripes being transversely spaced from each other by regions of relatively lower fibre entanglement density wherein the width of the stripes at the face of the fabric is less than the width of said regions of lower fibre entanglement density as measured transversely to the stripes.

According to a second aspect of the present invention there is provided a method of producing a bonded nonwoven fabric comprised of absorbent staple fibres comprising the steps of:

(i) providing an unbonded web comprising absorbent staple fibres, and (ii) forming in said unbonded web bonding stripes of relatively high fibre entanglement density extending along the fabric and into the fabric from at least one face thereof, said stripes being formed to have a width at the face of the fabric less than the transverse distance between the centre lines of adjacent stripes whereby there are regions of lower fibre entanglement density between the stripes as measured transversely thereto.

Bonded nonwoven fabrics in accordance with the invention have a quilted appearance by virtue of the stripes of high density fibre entanglement separated by regions (i.e. the "inter-stripe" regions) in which there is less fibre entanglement.

The nonwoven fabric has a combination of good strength and good absorbency and is particularly suitable for use as an absorbent layer in a wound dressing. The strength is achieved by virtue of the stripes of relatively high entanglement density whereas the absorbency is provided by the regions of lower fibre entanglement density provided between these stripes. Between the stripes, there may be some degree of fibre entanglement (produced during the bonding operation) but, if so, only to a lower degree than that provided in the stripes. In preferred embodiments of the invention, no bonding operation has been effected between the stripes.

The stripes of relatively high fibre entanglement density may be formed by a needling operation in which barbed ends of an array of barbed needles reciprocate into and out of the unbonded web to provide fibre entanglement in the regions (i.e. the stripes) where high fibre entanglement density is required, there preferably being no needling effected between the stripes. The needles in the array may be arranged in columns extending in the direction of relative movement of the unbonded web past the array.

The columns have a width which is less than the transverse spacing between the centre lines of adjacent columns. As such, passing the unbonded fabric relatively past the array so that it (the unbonded fabric) is effectively moving parallel to the columns results in parallel stripes of needling (the high density fibre entanglement regions) which are transversely spaced from each other by a width greater than that of the columns. In this "inter-stripe" spacing, it is preferred that no needling is effected (thereby to avoid reducing absorbency further), but we do not preclude the possibility of some degree of needling in these regions (e.g. using widely spaced needles).

For the purposes of the procedure described in the preceding paragraph, the widths of the columns are determined by the transverse spacing between the two outermost lying tips of the needle in the column (one of these tips being, of course, at one side of the column and the other tip being at the opposite side of the column).

Needle arrays for use in producing bonded fabrics in accordance with the invention may be produced by modification of commercially available needle boards, as explained in more detail below with reference to FIGS. 2, 3 and 4.

Alternatively, the needleboard may be a specially manufactured item having the required needle positions to produce stripes of the desired width and spacing. If this is a non-standard arrangement, stripper and penetration plates will also have to be manufactured to allow passage of the needles.

Bonded nonwoven fabrics in accordance with the invention may be such that the width of the stripes (providing the regions of relatively high density fibre entanglement) at the face of the fabric have a width of 0.05 mm to 4 mm, preferably 0.75 mm (or 1 mm) to 3 mm with a transverse distance between the longitudinal centrelines of adjacent stripes in the range 4 to 16 mm, more preferably 4 to 12 mm (e.g. about 4 mm to about 8 mm). Preferred bonded nonwoven fabrics in accordance with the invention has stripes with a 0.75 mm (or 1 mm) to 3 mm and an inter-stripe spacing of about 4 mm to about 8 mm. The stripes may be of substantially equal width at the face of the fabric and of substantially equal width throughout their depth. Generally, the stripes will be parallel to each other. Advantageously, the stripes may be oriented in the length direction (i.e. machine direction of the produced web) which ties the bonded nonwoven fabric (felt) together providing a greater overall strength.

The stripes may penetrate part—or the whole-way through the fabric. However it is preferable the stripes go the whole way through to provide sufficient strength.

Needling is the preferred method of producing the stripes which, as indicated above, are formed by the barbed ends of needles reciprocating into and out of one side of the fabric. Optionally, the fabric may additionally be needled from the other side of the fabric (referred to for convenience as the "reverse side"). Generally, needling of the reversed side would be effected using a full array of needles (rather than just an array producing stripes), in which case a low needle penetration depth and/or a low needling speed at the reverse side should be employed, otherwise the benefits of producing stripes at the front face of the fabric will be lost.

The weight of the nonwoven material may be 100-300 g m$^{-2}$. The unbonded web may, for example, be a cross-lapped web.

The invention is applicable to a wide range of absorbent fibres, e.g. as generally employed in the production of nonwoven fabrics for use as wound dressings. The absorbent fibres may, for example, comprise cellulose fibres (e.g. cotton or viscose (regenerated cellulose)), alginate, or carboxymethyl cellulose fibres are a blend of any two or more of these fibre types. The fibres may be alginate fibres incorporating (in the alginate fibres) a further polysaccharide (e.g. carboxymethyl cellulose) for the purpose of improving the absorbency of the fibres. Such fibres may, for example, be produced in accordance with the disclosure of U.S. Pat. No. 6,080,420.

The length of the staple fibres in the nonwoven material may for example be from a few millimetres, e.g. 3 mm, and up to a typical maximum of 120 mm. The staple length is preferably 37-76 mm. Increasing the length of fibres can improve strength as each fibre can have a greater degree of entanglement.

The absorbent fibres may have a composition such that the fibre gels on absorption of aqueous fluids.

A further possibility is that the fibres are superabsorbent fibres (e.g. polyacrylic acid fibres), but in this case it would generally be necessary to blend the superabsorbent fibres with fibres of lesser absorbency (e.g. absorbent fibres of the type discussed above or non-absorbent fibres to which reference is made below).

The nonwoven fabric may comprise non-absorbent fibres in addition to the absorbent fibres. The non-absorbent fibres may be resilient and serve to provide "structure" to the nonwoven fabric to help maintain good absorbency. Typical resilient fibres include polyester, polyamide (e.g. nylon) acrylic and polypropylene fibres. These fibres tend to have a greater strength than absorbent fibres and can therefore provide additional strength as well as bulk. If desired, the polyester and/or polypropylene fibres (if used may be in the form of bicomponent fibres wherein part of the fibre, for example the sheath in a sheath/core fibre, melts at a lower temperature than the core. This can further enhance strength and resiliency to the nonwoven material if the bicomponent fibre is activated by passing through a hot air oven or laminator. If a laminator is used, then care should be taken to ensure that excessive compression is not applied to the bonded nonwoven material, otherwise the benefits of the invention may be lost.

If the bonded nonwoven web of the invention is for use as an absorbent layer in a wound dressing, at least some of the absorbent fibres and/or at least some of the non-absorbent fibres (if present) that form the nonwoven material may incorporate an antimicrobial agent. Such an agent may be incorporated at the time the fibres are formed, may be applied to the fibres before they are formed into the initial non-bonded web, or may be applied to the final bonded web. Examples of antimicrobial agents that may be used include silver, silver based materials, copper, copper based materials, honey and biguanides (e.g. PHMB (polyhexamethylene biguanide)).

By way of example, alginate fibres may be produced by spinning an aqueous dope containing dissolved alginate (optionally also dissolved carboxymethyl cellulose in accordance with the teachings of U.S. Pat. No. 6,080,420) and also containing a silver compound into a coagulation bath containing calcium ions to form the fibres. Alternatively, fibres for use in forming the nonwoven material may be sprayed with, or dipped in, a solution containing the desired antimicrobial agent. A further possibility is that the final, bonded web is sprayed with, or dipped in, a solution containing the antimicrobial agent.

BRIEF DESCRIPTION OF THE DRAWINGS

The invention will be described by way of example only with reference to the accompanying drawings, in which.

DETAILED DESCRIPTION

Figure 1:
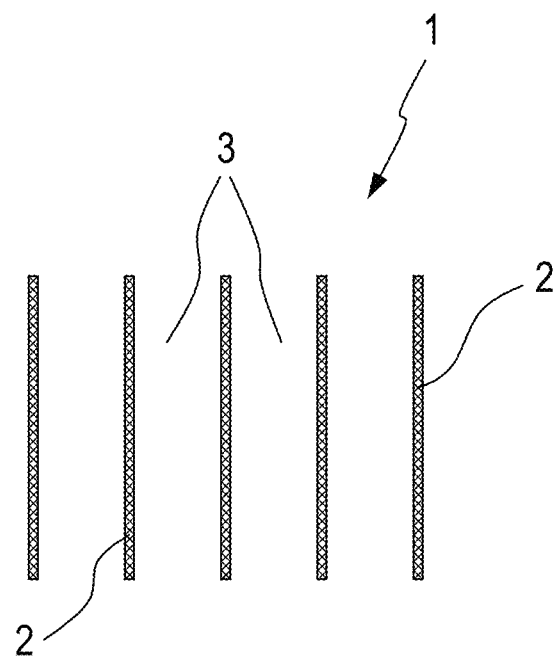
FIG. 1 represents a portion of one embodiment of non-woven fabric in accordance with the invention.

The embodiment of fabric 1 illustrated in FIG. 1 is a non-woven material (e.g. comprised of fibres of the composition and length discussed above) which is bonded by parallel stripes of needling 2. The regions 3 between the stripes are free of needling. Purely by way of example, the stripes 2 may have a width of about 1 mm and a spacing (as measured by the distance between their longitudinal centre-lines) of 8 mm, but other combinations of values are possible. Overall, the fabric 1 has a quilted construction, as provided by the needled stripes.

Figure 2:
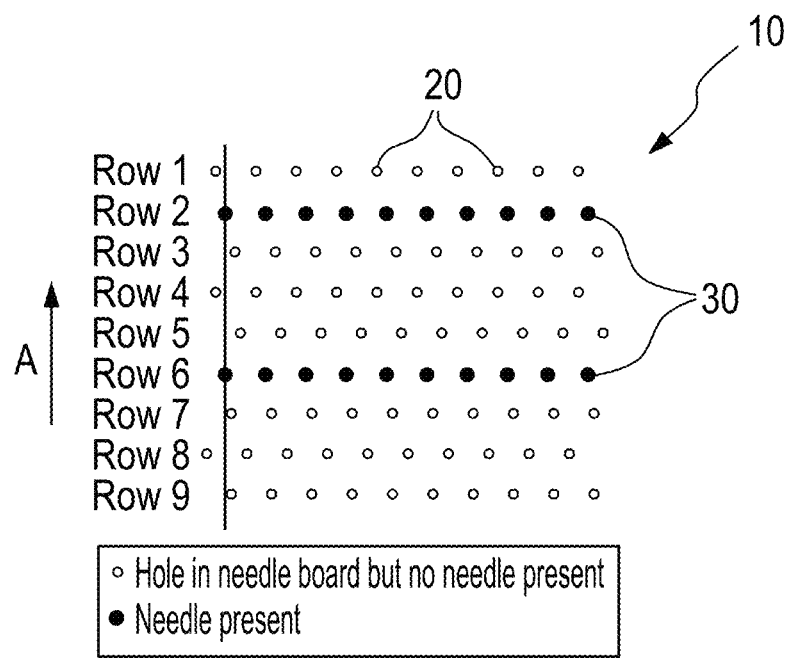
FIG. 2 schematically represents, to a much enlarged scale, a portion of a commercial needleboard.

Referring now to FIG. 2, there is schematically illustrated a portion of a commercially available needleboard 10 as adapted for use in producing a nonwoven fabric in accordance with the invention, e.g. a fabric as illustrated in FIG. 1. As well understood in the art, such a needleboard has an array of apertures in which needles may be removably mounted. Represented in FIG. 2 by open circles 20 are apertures where needles would normally be fitted but which have been removed for the purposes of adapting the needleboard for the present invention. Also shown in FIG. 2 are solid circles 30 representing apertures where needles will be retained in the apertures in the adaptation of the needleboard to produce a fabric in accordance with the invention. Generally speaking, the apertures are arranged in rows—illustrated in FIG. 2 as rows 1-9 although typically many more such rows would be present in the needleboard. A typical needleboard may for example comprise 32 rows of apertures with there being 172 apertures in each row. An example of such a needleboard that may be adapted for the purposes of the invention is available from TecTex and the invention will be further described with reference thereto.

In preparation of the bonded fabric, the nonwoven bonded material is moved relatively to the needleboard in the direction of arrow A.

The apertures 20, 30 in any one row are aligned with each other. Thus, for example, going from left to right along row 1, the centrelines of the apertures 20 lie on a straight line which is at right angles to the direction of arrow A. Additionally, the spacing between the holes in any one row is constant, usually a value in the range 6-12 mm. The uniformly spaced apertures in any one row are however staggered with respect to corresponding apertures in an immediately adjacent row.

Figure 3:
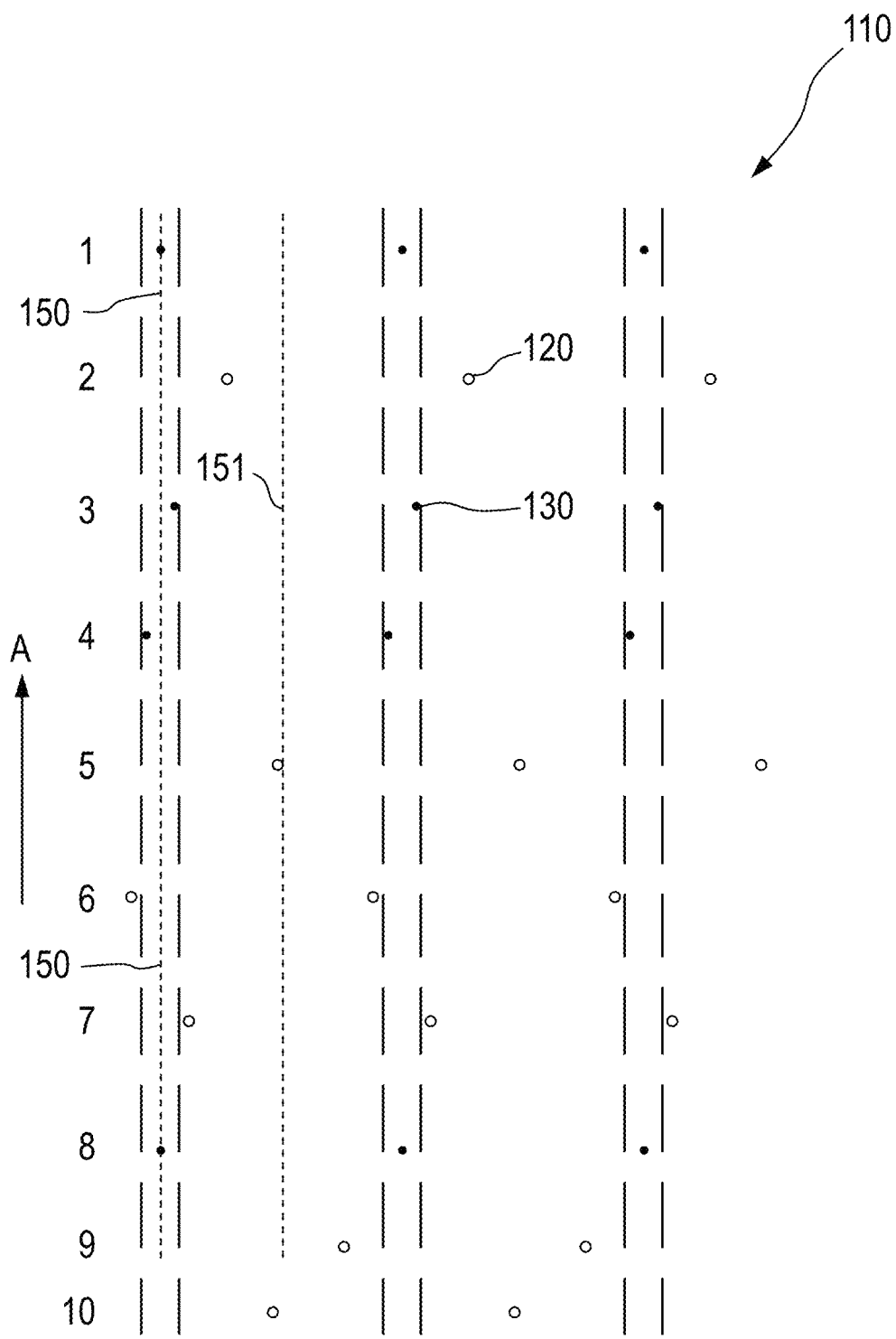
FIG. 3 schematically illustrates, to an even larger scale, a needleboard adapted for use in the invention.

This is explained more fully with reference to FIG. 3 which schematically illustrates, to a larger scale, a portion of a needleboard of a similar type to that illustrated in FIG. 2 but referenced as 110 and fitted with a pattern of needles to produce (by an otherwise conventional needling operation) a fabric 1 of the type shown in FIG. 1. The apertures in the needleboard 110 are represented either by open circles 120 or solid circles 130. The open circles 120 represent apertures where needles would normally be fitted but which are not present for the purposes of adapting the needleboard 110 for use in the present invention. The solid circles 130 represent apertures where barbed needles will be retained for the purposes of adapting the needleboard 110 to produce the fabric 1. (In the following description, reference numeral 130' is used to identify a needle itself). For the purposes of the following explanation, it is assumed that the location of the needles 130' (i.e. in the apertures represented by the solid circles) is such as to produce a fabric 1 in which the stripes 2 have a width of 1 mm and a spacing (between the longitudinal centre lines of adjacent stripes) of 8 mm, so that between adjacent stripes there is an "un-needled" region having a width of 7 mm. However, this particular configuration is mentioned purely for the purposes of simplicity and other configurations (to which reference is made below) are possible.

The apertures 120, 130 in any one row are aligned with each other along the length of the row (i.e. in the direction transverse to arrow A). Thus, for example, going from left to right along row 1 of needleboard 110, the centre lines of the apertures 130 lie on a straight line. Similarly for the apertures 120 in row 2, and for all other rows. Additionally, the spacing between the apertures 120 or 130 (as the case may be) in any one row is constant. For the purposes of the present explanation, that spacing is assumed to be 8 mm but more generally could be in the range of 6-12 mm in other embodiments of needleboard. The spacing between adjacent rows (e.g. between rows 1 and 2 or between rows 2 and 3 etc.) is for simplicity also shown as being constant for the majority of the rows, with a value, say, in the range of 6-12 mm. However, in other embodiments of needleboard, the inter-row spacing may vary (e.g. within the range 6-12 mm) and this is illustrated in FIG. 3 by the reduced spacing between Rows 8 and 9 and between Rows 9 and 10. It should at this point be noted that the inter-row spacing does not affect the width of the needled stripes 2 in the fabric 1, nor the spacing between such stripes.

As mentioned above, the apertures 120 or 130 (as the case may be) in any one row are aligned with each other. However, the apertures 120 or 130 in any one row are staggered with respect to apertures in the adjacent row. Thus, reference to FIG. 3 shows that the apertures 130 in row 1 are staggered relative to the apertures 120 in Row 2 which in turn are staggered with respect to apertures 130 in row 3, and so on, although certain rows (e.g. rows 1 and 8 illustrated in FIG. 3) may have aligned apertures. In the case of "normal" use of the needleboard 110, needles would occupy all of the apertures 120 and 130 and the offsets in the needles (as between adjacent rows) create a randomization effect to present repetitive patterns appearing in the finished non-woven material. It is however the presence of these offsets as between apertures 120 and 130 in adjacent rows and also the fitting of needles 130' to some, but not all, apertures that are used to advantage for the purposes of implementation of the present invention, as will be understood from the more detailed description given below.

As mentioned, the apertures 120 or 130 in any one row have an equal spacing (assumed to be 8 mm for the purposes of the present description). Also as mentioned, the apertures 120 or 130 in any one row are staggered relative to those in an adjacent row. Therefore, in view of these relationships, the position of the $1^{st}, 2^{nd}, 3^{rd}, \ldots n^{th}$ apertures 120 or 130 in each row counting from the left-hand edge of the needleboard 110 (depicted in FIG. 3 by reference numeral 140) is a different distance from that of the corresponding ($1^{st}, 2^{nd}, 3^{rd} \ldots n^{th}$) apertures 120 or 130 in the immediately adjacent row.

For the purposes of further explanation, consider now that the positions of apertures 130 in Row 1 define "reference positions" for describing the locations of apertures 120 or 130 in other rows. FIG. 3 shows a notional reference line 150 that is drawn through the centre of the first (i.e. leftmost as seen in FIG. 3) aperture 130 in the first row, notional reference line 150 being drawn perpendicular to the needle rows in the plane of the paper. Similar notional reference lines 150 could be drawn through every other aperture 130 in the first row but are omitted for the purposes of simplicity. Nevertheless it should be appreciated that the comments made below in relation to the illustrated notional reference line 150 (drawn through the leftmost aperture 130 of the first row) are generally applicable to a similar notional reference line drawn through any other aperture 130 of the first row.

Given the staggering between apertures in adjacent rows, it will be appreciated that the first aperture in each row of apertures either lies (a) to the left of notional reference 150 (see rows 4 and 6), (b) to the right of notional reference line 150 (e.g. see rows 2 and 7) or (c) (in certain cases) actually on the notional reference line 150 (e.g. see row 8). Consider now those (first) apertures in the various rows that lie either to the left or to the right of notional reference line 150. Some might, for example, have a centre 0.5 mm to one side (or the other) of reference line 150. Additionally there may be some apertures with their centres 1 mm to one side (or the other) of reference line 150. There will also be apertures with their centres 4 mm from reference line 150 (although these may be apertures to the right of line 150 rather than to the left). There will also be apertures at distances from reference line 150 other than 0.5 mm, 1 mm and 4 mm, but these three values have been selected for the purposes of further describing specific embodiments of the invention.

Assume now that the fabric 1 to be produced is the one described above in which the stripes 2 have a width of 1 mm and a spacing (between the longitudinal centre lines of adjacent stripes) of 8 mm. To produce such a fabric, needles 130' are fitted in all of the apertures 130 in the first aperture row. Additionally, further rows are now identified in which the leftmost aperture lies on centre line 150 and needles 130' are fitted into all of the apertures 130 for each such row identified. Purely for the purposes of illustration, an additional such row (for which the centres of apertures 130 fall on reference line 150) is considered in FIG. 3 to be row 8. Furthermore, additional rows are identified for which the leftmost aperture is 0.5 mm or less to either side of notional centreline 150. Needles 130' are fitted in the apertures 130 of all such rows identified. Purely for the purpose of illustration, these rows are identified in FIG. 3 as rows 3 and 4. Thus in the portion of needleboard 110 illustrated in FIG. 3, needles 130' are fitted in rows 1, 3, 4 and 8 (effectively producing "bands" of needles 131 parallel to arrow A) to producing the desired fabric. It will however be appreciated that the needleboard contains many additional rows (e.g. a total of 32) and needles will also be fitted to certain of the rows not illustrated in FIG. 3

The needleboard 110 fitted with needles in accordance with the layout described in the previous paragraph is then used for needling a fabric in an otherwise conventional needling operation by reciprocating the barbed needles into and out of the material to be needled whilst that material is passing in the direction of arrow A relatively past the needle rows. It will be appreciated from the foregoing description that the needle pattern results in the production of a needled fabric 1 in which the stripes 2 have a width of 1 mm (as determined by the fact that the needles 130 either lie on the reference line 150 or a maximum of 0.5 mm to either side thereof) and that the stripes have a spacing (between their longitudinal centrelines) of 8 mm as determined by the equivalent spacing (i.e. 8 mm) between the centres of the apertures in any one row.

It will be further appreciated from the foregoing description that fabrics 1 with stripes 2 with an inter-stripe spacing of 8 mm but a width other than 1 mm may be prepared by a modification of the configuration of needles 130' in the needleboard 110. Consider the case where the fabric is to have stripes 2 with a width of a 2 mm and a spacing of 8 mm (as between the longitudinal centre lines of adjacent stripes 2). In this case, the needleboard 110 described above for production of a fabric with stripes 2 having a width of 1 mm may be fitted with additional needles. More specifically, additional rows in the needleboard are identified for which the centres of the leftmost apertures are 1 mm or less to the left or right of notional reference line 150. Needles 130 are then fitted to all apertures 120 in the rows identified. The modified needleboard 110 may then be used for producing the desired fabric in the manner outlined above.

It is further possible to modify the needleboard to produce a fabric 1 with stripes 2 having a spacing (between the longitudinal centre lines of adjacent stripes) of 4 mm, with each stripe having, say, a width of 1 mm. To do so, the needleboard 110 configured for producing the fabric with stripes 2 having a width of 1 mm and an inter-stripe spacing (between the longitudinal centre lines of adjacent stripes) of 8 mm may be fitted with additional needles 130 in the following manner. Rows are identified having apertures that lie on or within 0.5 mm either side of a notional reference line 151 that is drawn midway between the apertures in row 1. Needles are fitted to all apertures in the additionally identified rows. This effectively provides columns of needles that will produce stripes of width 1 mm with there being an inter-stripe spacing (between the longitudinal centre lines of adjacent stripes) of 4 mm.

It will be appreciated from the foregoing description that many other modifications are possible. Thus, for example, the procedures described above may readily be adapted to produce fabrics 1 with stripes 2 having an inter-stripe spacing (between the centre lines of adjacent stripes) of 12 mm, with the individual stripes 2 having a width (say) of 1 mm, 2 mm or 3 mm as desired. Furthermore, the above described procedures are applicable to needleboards in which the spacing between individual apertures is other than 8 mm. Thus, for example, the invention is applicable to needleboards 110 in which this spacing is 6 mm, thus readily leading to the production of fabrics 1 with stripes 2 having an inter-stripe spacing of 6 mm.

To illustrate further the above discussion of FIG. 3, Table 1 below (which is to be considered in conjunction with FIG. 4) gives for a needleboard having 32 rows (and considered to be viewed in the same manner as FIGS. 2 and 3) the distance of the leftmost aperture in each row from the left-hand edge of the needleboard.

TABLE 1

| Row No. | Distance |
| --- | --- |
| 1 | 6.5 |
| 2 | 4.75 |
| 3 | 10 |
| 4 | 5.75 |
| 5 | 9.75 |
| 6 | 4 |
| 7 | 10.25 |
| 8 | 6.75 |
| 9 | 10.75 |
| 10 | 5.25 |
| 11 | 8.75 |
| 12 | 4.25 |
| 13 | 7.5 |
| 14 | 6.25 |
| 15 | 11 |
| 16 | 9 |
| 17 | 4.5 |
| 18 | 7 |
| 19 | 9.25 |
| 20 | 7.75 |
| 21 | 5.5 |
| 22 | 8.5 |
| 23 | 6 |
| 24 | 11.5 |
| 25 | 7.25 |
| 26 | 10.5 |
| 27 | 8.25 |
| 28 | 11.75 |
| 29 | 5 |
| 30 | 9.5 |
| 31 | 11.25 |
| 32 | 8 |

Figure 4:
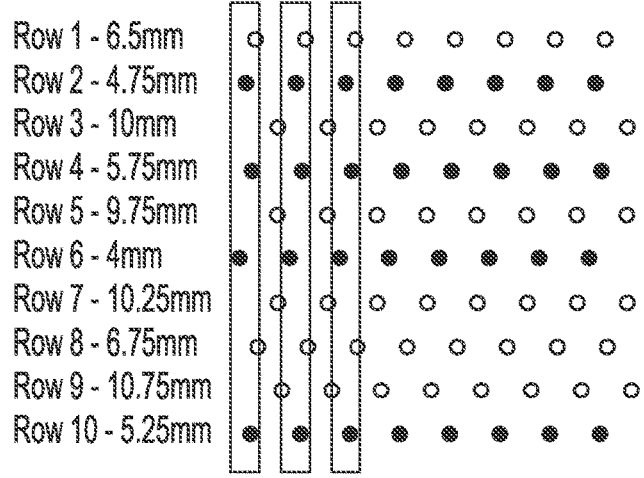
FIG. 4 schematically represents, to a much enlarged scale, a portion of a commercial needleboard showing spacing of needles from an edge of the needleboard.

For the purposes of clarity, FIG. 4 shows rows 1-6 of the needleboard and, for each of these rows, includes the distance of the centre of the leftmost aperture from the left-hand edge of the needleboard.

The spacing of the centres of the apertures in any one row is constant and for the purpose of the following discussion is considered to be 8 mm, each row having a total of 172 needles.

To produce a fabric of the type shown in FIG. 1 with a 2 mm (nominal) wide needled stripe, the needleboard is provided with needles in all of the apertures in each of the following rows:

Row 2 (4.75 mm)
Row 4 (5.75 mm)
Row 6 (4 mm)
Row 10 (5.25 mm)
Row 12 (4.25 mm)
Row 17 (4.5 mm)
Row 21 (5.5 mm)
Row 24 (11.5 mm)
Row 28 (11.75 mm)
Row 29 (5 mm)

(The figures in parentheses represent the distance of the leftmost aperture in the row from the left-hand edge of the needleboard).

Excluding rows 24 and 28, the spacing of the left-most apertures from the edge of the needleboard ranges from 4 mm to 5.75 mm, a difference of 1.75 mm. For rows 24 and 28, for which the leftmost apertures initially appear to have a large distance from the left-hand edge of the needleboard, the first (i.e. leftmost) needle in these rows will actually correspond with the second needle of the other selected rows. The needle stripe produced from the first needles in all rows (but excluding rows 24 and 28) will have a width of 1.75 mm (determined by the position of the needles in rows 4 and 6). All other needle stripes (which will be produced using all of the selected needles will have a width of 2.25 mm, determined by the positions of the needles in rows 4 and 28. Thus, the arrangement of needles provides stripes with a nominal width of 2 mm (0.25 mm is negligible distance in this context).

The widths of the shaded rectangles in FIG. 4 represent the widths of needle stripes produced by the described needle arrangement.

Figure 5:
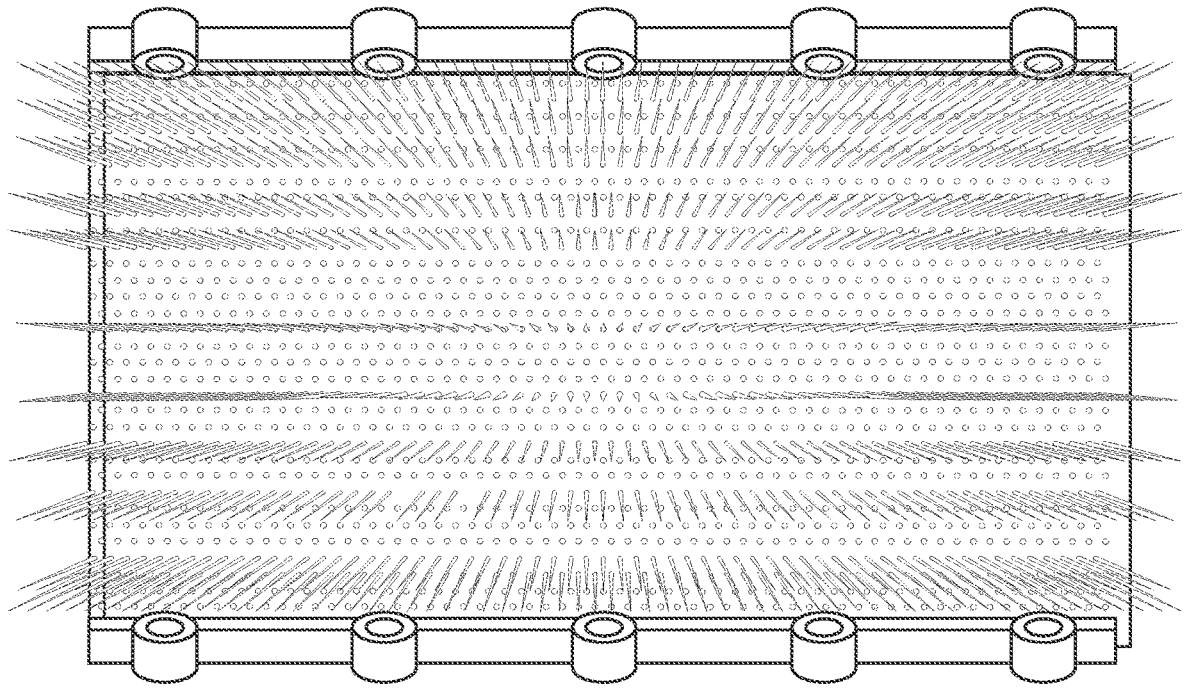
FIG. 5 shows a representation of a photograph of a needleboard set-up for producing a fabric in accordance with the invention.

FIG. 5 shows a representation of a photograph of a working embodiment of needleboard embodying the principles described above. Fabric to be needled moves in the direction of arrow A (FIG. 3) relatively passed the needleboard. The needles are arranged, in the manner described above, to produce stripes of needling. As it will be appreciated from FIG. 5, the spacing of the various holes in the needleboard (into which barbed needles may be inserted) is not constant and certain rows are closer to each other than others.

The invention has been described above with particular reference to the use of needling to provide entanglement of fibres to provide the stripes and thereby form the bonded non-woven fabric. It should however be appreciated that other means of effecting entanglement could be employed using the same principles as described above. Thus, for example, fine water jets could be employed as the means for entangling fibres, the water jets being arranged in accordance with the principles described above in relation to needles.

The invention will be illustrated with reference to the following non-limiting Examples.

General

In the following Examples, bonded fabrics in accordance with the invention were produced from (unbonded) nonwoven webs formed of alginate fibres containing carboxymethyl cellulose. The alginate fibres consisted of High Guluronic alginate, were cut to staple length of 50 mm and had thickness of 2-2.5 dtex. The target weight of the unbounded web was 200 g/m².

All Examples used the same nonwoven needling line which had two needlelooms. Needleloom 1 (NL1) needled from the top, and Needleloom 2 (NL2) needled from underneath. NL1 was manufactured by TecTex and had the capability to mount 32 rows of needles with 172 needles per row. The aperture configuration was as set out in Table 1 above (the spacing between the apertures in any one row was 8 mm and the spacing between rows was 6-12 mm. Only the needle pattern on NL1 was changed (various rows of needles being selected to provide stripes of desired width).

The needling speeds given in the Examples are a machine setting and assume the NL1 needleboard is completely filled with needles. Therefore, the actual punch density is lower, and will be the ratio of the number of rows of needles used compared to 32 rows when the needleboard is full, i.e. in Example 1, the actual punch density of NL1 will be 6/32× 200=~38 punches/cm².

EXAMPLE 1

Needleloom NL1 was set-up so that needles were only present in the following 6 rows 2, 6, 12, 17, 24 and 28 (all needles in any one of these rows being present).

The unbonded fabric (weight 200 g m²) was passed through the needling line which was operated with the following conditions:

NL1 used a penetration depth of 7 mm at speed of 200 punches/cm².

NL2 used a penetration depth of 4 mm at speed of 40 punches/cm$^2$.

The resulting fabric had stripes of needling with a width of 1.25 mm and with a spacing of 8 mm between the centrelines of the stripes.

Properties of the bonded fabric were as follows:
Absorbency=33 g/100 cm$^2$,
Dry Strength=3.0 N/cm, and
Wet Strength=1.5 N/cm.

EXAMPLE 2

Needleloom NL1 was set-up so that needles were present in all apertures of the following 8 rows 2, 6, 10, 12, 17, 24, 28 and 29. This was to give a pattern of 1.75 mm stripes having 8 mm spacing between their centrelines. This was 2 additional rows compared to example 1.

The unbonded fabric (weight 200 g m$^{-2}$) was passed through the needling line with NL1 operated to provide a penetration depth of 7 mm at speed of 200 punches/cm$^2$.

The parameters of NL2 were varied using a combination of penetration depths of 2, 4 and 6 mm, each with a speed of 40, 60 and 80 punches/cm$^2$, thereby providing a total of nine samples, for which the properties (taken overall) were as follows:
Absorbency=33-40 g/100 cm$^2$,
Dry Strength=1.2-3.7 N/cm, and
Wet Strength=1.2-3.2 N/cm.

EXAMPLE 3

Needleloom NL1 was set up so that needles were present in following 10 rows 2, 4, 6, 10, 12, 17, 21, 24, 28 and 29. This was to give a pattern of 2.25 mm stripes having 8 mm spacing between their centrelines. This was an additional 2 rows compared with Example 2.

The needle line was operated with the following conditions:

NL1 used a penetration depth of 7 mm at speed of 200 punches/cm$^2$.

NL2 used a penetration depth of 2 mm at speed of 80 punches/cm$^2$.

The strength of the web was, according to a subjective assessment, considered to be sufficient.

EXAMPLE 4

Needleloom NL1 was set up so that needles were present in following 12 rows 2, 4, 6, 10, 12, 15, 17, 21, 24, 28, 29 and 31. This was to give a pattern of 2.75 mm stripes having 8 mm spacing between their centrelines. This was an additional 2 rows compared with Example 3.

NL1 used a penetration depth of 7 mm at speed of 200 punches/cm$^2$.

NL2 used a penetration depth of 2 mm at speed of 80 punches/cm$^2$.

The strength of the web was, according to a subjective assessment, considered to be sufficient.

EXAMPLE 5

On NL1 using rows of needles of 1, 5, 6, 9, 11, 13, 16, 17, 21, 22, 27 & 31 gave a pattern of 1.0 mm wide stripes of needling with 4 mm spacing between their centres.

NL1 used a penetration depth of 7 mm at speed of 200 punches/cm$^2$.

NL2 used a penetration depth of 2 mm at speed of 80 punches/cm$^2$.

For a particular application Examples 3, 4 and 5 were considered to still have sufficient strength. This was assessed subjectively.

The strength of the web was, according to a subjective assessment, considered to be sufficient.

EXAMPLE 6

This Example was effected using an unbonded fabric comprised of the alginate fibres containing carboxymethyl cellulose (CMC) cross-lapped with a 17 g m$^{-2}$ nylon spunbonded material. The nominal weight of the material to be bonded (including spunbonded material) was 200 g m$^{-2}$.

The needle arrangement was as in Example 3.

NL1 was operated to provide a penetration depth of 7 mm at a speed of 200 punches/cm$^2$. NL2 was turned off.

Properties of the bonded fabric were as follows:
Absorbency=36 g/100 cm$^2$,
Dry Strength=7.4 N/cm, and
Wet Strength=3.8 N/cm.

The following numbered embodiments are included in the present application:

Embodiment 1. A bonded nonwoven fabric comprised of absorbent staple fibres and having bonding stripes of relatively high fibre entanglement density extending along the fabric and into the fabric from at least one face thereof, said stripes being transversely spaced from each other by regions of relatively lower fibre entanglement density wherein the width of the stripes at the face of the fabric is less than the width of said regions of lower fibre entanglement density as measured transversely to the stripes.

Embodiment 2. A fabric according to embodiment 1 wherein the width of the stripes at the face of the fabric is 0.5 mm to 4 mm.

Embodiment 3. A fabric according to embodiment 2 wherein the width of the stripes at the face of the fabric is 0.7 mm to 3 mm.

Embodiment 4. A fabric according to any one of embodiments 1 to 3 wherein the transverse distance between the longitudinal centre lines of adjacent stripes is in the range 4 to 16 mm.

Embodiment 5. A fabric according to embodiment 4 wherein the transverse distance between the longitudinal centre lines of adjacent stripes is in the range 4 to 12 mm.

Embodiment 6. A fabric according to embodiment 5 wherein the transverse distance between the longitudinal centre lines of adjacent stripes is in the range 4 to 8 mm.

Embodiment 7. A fabric according to any one of embodiments 1 to 6 wherein the stripes are of substantially equal width at the face of the fabric.

Embodiment 8. A fabric according to any one of embodiments 1 to 7 wherein the stripes are of substantially equal width throughout their depth.

Embodiment 9. A fabric according to any one of embodiments 1 to 8 wherein the staple absorbent fibres have a length of 25 to 76 mm.

Embodiment 10. A fabric according to any one of embodiments 1 to 9 wherein the absorbent fibres comprise viscose, cotton, alginate or carboxymethyl cellulose fibres or a blend of any two or more of these fibre types.

Embodiment 11. A fabric according to any one of embodiments 1 to 9 wherein the fibres are alginate fibres incorporating carboxymethyl cellulose.

Embodiment 12. A fabric according to any one of embodiments 1 to 9 wherein the absorbent fibres comprise gelling fibres.

Embodiment 13. A fabric according to any one of embodiments 1 to 9 wherein the absorbent fibres comprise superabsorbent fibres.

Embodiment 14. A fabric according to any one of embodiments 1 to 13 additionally comprising non-absorbent staple fibres.

Embodiment 15. A fabric according to embodiment 14 wherein the non-absorbent staple fibres have a length of 25 to 76 mm.

Embodiment 16. A fabric according to embodiments 14 or 15 wherein the non-absorbent fibres are resilient.

Embodiment 17. A fabric according to any one of embodiments 14 to 16 wherein the non-absorbent fibres are selected from polyester, polyamide, acrylic or polypropylene fibres or a blend of two or more of these fibre types.

Embodiment 18. A fabric according to any one of embodiments 1 to 17 having a basis weight of 100 to 300 g m$^{-2}$.

Embodiment 19. A fabric according to any one of embodiments 1 to 18 wherein at least some of the absorbent fibres and/or at least some of the non-absorbent fibres (if present) incorporate an antimicrobial agent.

Embodiment 20. A fabric according to embodiment 19 wherein the antimicrobial agent is a silver compound.

Embodiment 21. A fabric according to embodiment 19 wherein the antimicrobial agent is a copper compound.

Embodiment 22. A fabric according to embodiment 19 wherein the antimicrobial agent is honey.

Embodiment 23. A fabric according to embodiment 19 wherein the antimicrobial agent is a biguanide.

Embodiment 24. A fabric according to embodiment 19 wherein the biguanide is poly(hexamethylene biguanide).

Embodiment 25. A fabric according to any one of embodiments 1 to 24 wherein the stripes have been formed by needling.

Embodiment 26. A wound dressing comprising a fabric according to any one of embodiments 1 to 25.

Embodiment 27. A method of producing a bonded nonwoven fabric comprised of absorbent staple fibres comprising the steps of:
(i) providing an unbonded web comprising absorbent staple fibres, and
(ii) forming in said unbonded web bonding stripes of relatively high fibre entanglement density extending along the fabric and into the fabric from at least one face thereof, said stripes being formed to have a width at the face of the fabric less than the transverse distance between the centre lines of adjacent stripes whereby there are regions of lower fibre entanglement density between the stripes as measured transversely thereto.

Embodiment 28. A method according to embodiment 27 wherein the bonding stripes are formed by a needling operation in which barbed ends of an array of barbed needles reciprocate into and out of the unbonded fabric as the latter is moved relatively past the array, wherein the needles in the array are arranged in columns extending in the direction of said relative movement, and wherein the column widths, as defined for any one column by the maximum transverse spacing of the needles therein, are less than the transverse spacing between the centre lines of adjacent columns.

Embodiment 29. A method according to embodiment 27 for use in producing a bonded nonwoven fabric as according to any one of embodiments 1 to 24.

It will be understood that the invention has been described by way of example only and modifications may be made whilst remaining within the scope and the spirit of the invention.

The invention claimed is:

1. A bonded nonwoven fabric comprising:
   absorbent staple fibres, wherein the absorbent staple fibres comprise gelling fibres, and
   bonding stripes extending along the bonded nonwoven fabric and into the bonded nonwoven fabric from at least one face thereof, wherein the bonding stripes are formed of needle bonded web, said bonding stripes being transversely spaced from each other by regions of unbonded web, which are free of needling, wherein:
   the bonding stripes are of high fibre entanglement density relative to the regions of unbonded web; and
   the width of the bonding stripes at the face of the bonded nonwoven web is less than the width of said regions of unbonded fabric as measured transversely to the bonding stripes.

2. The bonded nonwoven fabric as claimed in claim 1 wherein the width of the bonding stripes at the face of the bonded nonwoven fabric is 0.5 mm to 4 mm.

3. The bonded nonwoven fabric as claimed in claim 1 wherein the transverse distance between the longitudinal centre lines of adjacent bonding stripes is in the range 4 to 16 mm.

4. The bonded nonwoven fabric as claimed in claim 1 wherein the bonding stripes are of substantially equal width at the face of the bonded nonwoven fabric.

5. The bonded nonwoven fabric as claimed in claim 1 wherein the bonding stripes are of substantially equal width throughout their depth.

6. The bonded nonwoven fabric as claimed in claim 1 wherein the absorbent staple fibres have a length of 25 to 76 mm.

7. The bonded nonwoven fabric as claimed in claim 1 wherein the gelling fibres comprise alginate and/or carboxymethyl cellulose fibres.

8. The bonded nonwoven fabric as claimed in claim 1 wherein the gelling fibres are alginate fibres incorporating carboxymethyl cellulose.

9. The bonded nonwoven fabric as claimed in claim 1 additionally comprising non-absorbent staple fibres.

10. The bonded nonwoven fabric as claimed in claim 9 wherein the non-absorbent staple fibres are resilient.

11. The bonded nonwoven fabric as claimed in claim 9 wherein the non-absorbent staple fibres are selected from polyester, polyamide, acrylic or polypropylene fibres or a blend of two or more of these fibre types.

12. The bonded nonwoven fabric as claimed in claim 1 having a basis weight of 100 to 300 g m-2.

13. The bonded nonwoven fabric as claimed in claim 1 wherein at least some of the absorbent staple fibres incorporate an antimicrobial agent.

14. The bonded nonwoven fabric as claimed in claim 13 wherein:
   the antimicrobial agent is a silver compound; or
   a copper compound; or
   honey; or
   a biguanide.

15. The bonded nonwoven fabric as claimed in claim 1 further comprising non-absorbent staple fibres and wherein at least some of the absorbent staple fibres and/or at least some of the non-absorbent staple fibres incorporate an antimicrobial agent.

16. The bonded nonwoven fabric as claimed in claim 1 wherein the absorbent staple fibres further include cotton and/or viscose fibres.

17. A wound dressing comprising the bonded nonwoven fabric as claimed in claim 1.

18. A method of producing a bonded nonwoven fabric comprised of absorbent staple fibres comprising the steps of:
(i) providing an unbonded web comprising absorbent staple fibres comprising gelling fibres, and
(ii) forming in said unbonded web bonding stripes extending along the bonded nonwoven fabric and into the bonded nonwoven fabric from at least one face thereof, said bonding stripes being formed to have a width at the face of the bonded nonwoven fabric less than the transverse distance between the centre lines of adjacent bonding stripes whereby there are regions of unbonded web remaining between the bonding stripes as measured transversely thereto; wherein the bonding stripes are of high fibre entanglement density relative to the regions of unbonded web said bonding stripes being transversely spaced from each other by regions of unbonded web wherein the width of the bonding stripes at the face of the bonded nonwoven fabric is less than the width of said regions of unbonded web as measured transversely to the bonding stripes; and wherein the bonding stripes are formed by needling the unbonded web.

19. The method as claimed in claim 18 wherein the bonding stripes are formed by a needling operation in which barbed ends of an array of barbed needles reciprocate into and out of the unbonded web as the latter is moved relatively past the array, wherein the needles in the array are arranged in columns extending in the direction of said relative movement, and wherein the column widths, as defined for any one column by the maximum transverse spacing of the needles therein, are less than the transverse spacing between the centre lines of adjacent columns.

* * * * *